US 7,747,057 B2

(12) United States Patent
Wu et al.

(10) Patent No.: US 7,747,057 B2
(45) Date of Patent: Jun. 29, 2010

(54) METHODS AND APPARATUS FOR BIS CORRECTION

(75) Inventors: Xiaoye Wu, Rexford, NY (US); Paavana Sainath, Oconomowoc, WI (US); Thomas Louis Toth, Brookfield, WI (US); Thomas John Myers, Wauwatosa, WI (US); Mary Sue Kulpins, Brookfield, WI (US); Xiangyang Tang, Waukesha, WI (US); Roy-Arnulf Helge Nilsen, Menomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 771 days.

(21) Appl. No.: 11/442,450

(22) Filed: May 26, 2006

(65) Prior Publication Data

US 2007/0274581 A1 Nov. 29, 2007

(51) Int. Cl.
*G06K 9/00* (2006.01)
*G01N 23/00* (2006.01)

(52) U.S. Cl. .................... 382/131; 382/128; 378/21; 128/920

(58) Field of Classification Search ............ 378/4, 378/8, 901, 18, 19, 21, 23; 382/128, 130, 382/131, 132
See application file for complete search history.

(56) References Cited

U.S. PATENT DOCUMENTS

| 6,115,487 | A | 9/2000 | Toth et al. ............... 382/131 |
| 2004/0109528 | A1* | 6/2004 | Nukui et al. ............. 378/19 |
| 2005/0002484 | A1* | 1/2005 | Wu et al. .................. 378/4 |
| 2005/0249431 | A1* | 11/2005 | Ruhmschopf ............. 382/274 |
| 2006/0159223 | A1* | 7/2006 | Wu et al. .................. 378/18 |
| 2007/0268997 | A1* | 11/2007 | Zhu et al. ................. 378/7 |

OTHER PUBLICATIONS

J. Hsieh et al., "An Iterative approach to the beam hardening correction in cone beam CT", Medical Physics, Jan. 2000, pp. 23-29, vol. 27, No. 1.*
R. Ning et al., "X-Ray Scatter Suppression Algorithm for Cone Beam Volume CT", Proceedings of SPIE 2002, pp. 774-781, vol. 4682. cited by other.*
Kachelrieb, M.; Kalender, W.A., "Improving PET/CT attenuation correction with iterative CT beam hardening correction" Nuclear Science Symposium Conference Record, 2005 IEEE vol. 4, Oct. 23-29, 2005 pp. 5 pp.*
Joseph et al. "A method for simultaneous correction of spectrum hardening artifacst in CT images containing both bone and iodine" Med. Phys. 24 (10) Oct. 1997.*

* cited by examiner

*Primary Examiner*—Andrew W Johns
*Assistant Examiner*—Tahmina Ansari
(74) *Attorney, Agent, or Firm*—ZPS Group, SC (57) ABSTRACT

A method for performing BIS correction includes scanning an object with a computed tomography (CT) system to obtain data, reconstructing an image using the obtained data, and using the image to perform BIS correction.

20 Claims, 5 Drawing Sheets

Uncorrected Image

FIG 6

Corrected Image

METHODS AND APPARATUS FOR BIS CORRECTION

BACKGROUND OF THE INVENTION

This invention relates generally to methods and apparatus for computed tomography (CT), and more particularly to methods and apparatus that provide for Bone Induced Spectral (BIS) artifact correction.

BIS artifacts are produced due to differential beam hardening owing to the presence of bone in an object being scanned. These artifacts cannot be corrected or accounted for using the traditional water based beam hardening correction. The non-linear spectral response in the detector can be characterized and corrected as long as the amount of bone in the object being scanned can be measured.

A significant artifact can be produced by a relatively small error in the projections. Like most CT artifacts, the center of the field of view of the detector is most sensitive to BIS artifacts.

Therefore, described below are methods and apparatus for correcting for BIS artifacts in the image space.

BRIEF DESCRIPTION OF THE INVENTION

In one aspect, a method for performing BIS correction is provided. The method includes scanning an object with a computed tomography (CT) system to obtain data, reconstructing an image using the obtained data, and using the image to perform BIS correction.

In another aspect, a cone beam computed tomography (CT) system is provided. The system includes a radiation source configured to emit a cone beam of radiation, a detector positioned to receive the cone beam, and a computer coupled to the source and detector. The computer is configured to receive data from the detector, reconstruct an image using the obtained data, and use the image to perform BIS correction.

In still another aspect, a computer readable medium is embedded with a program configured to instruct a computer to use an image to perform BIS correction without using a total projection length of bone and water.

DETAILED DESCRIPTION OF THE INVENTION

There are herein provided BIS correction methods and apparatus useful for imaging systems such as, for example, but not limited to a Computed Tomography (CT) System. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

2

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 1:
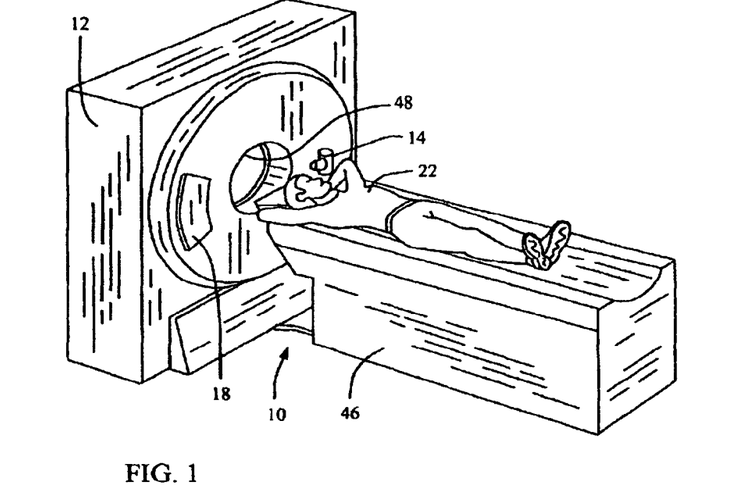
FIG. 1 is a pictorial view of a CT imaging system embodiment.
Figure 2:
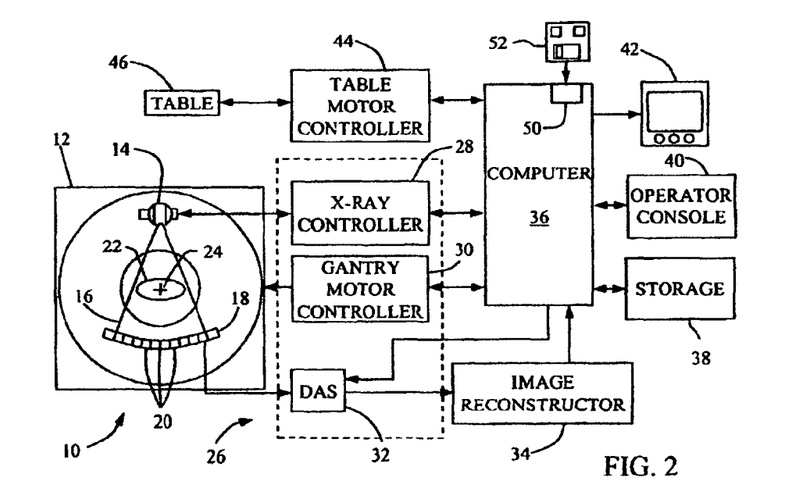
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12. Although, represented as a third generation CT system, system 10 could be any type of imaging system including a combined PET/CT system wherein PET is Positron Emission Tomography, and it is contemplated that the benefits of the invention accrue to all diagnostic imaging systems.

Detector array 18 is formed by a plurality of detector rows (not shown in FIGS. 1 and 2) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via a console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28, and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center. Additionally, although described in a human patient setting it is contemplated that the benefits of the invention accrue to non-human imaging systems such as those used to image animals.

In one embodiment, CT system 10 is a Cone Beam Multi-Slice Computed Tomography (CT) System 10 in that radiation source 14 is configured to provide a Cone Beam of x-rays through object 22 and onto multislice detector array 18.

Regarding water and bone beam hardening, a spectral calibration is based on modeling the physical response of the system by using the measured signal at different beam energies. The efficiency of the detector element as a function of incident X-ray energy is computed from the gain response of the air scans at different energies. The water beam hardening correction is then derived by taking the gain response and computing the projection value through water. Similarly, an additional computation can be used to derive the water+bone projection value. Both the water beam hardening and the water+bone beam hardening values can then expressed as polynomial coefficients.

Effectively, the response of each detector pixel is modeled based on knowledge of the input x-ray spectrum, for an object with a water path length $w_l$ and bone path length of $b_l$.

The ideal value is a linear function of the length through water and the length through bone:

$$p_{ideal} = \mu_w \times w_l + \mu_b \times b_l$$

Where: $\mu_w$=linear attenuation coefficient for water, and $\mu_b$=linear attenuation coefficient for bone.

Further, $\Delta = p_{ideal} - p_t$ is then computed, with $p_t$ derived from the air scan data, where $p_t$ is the computed total projection value after water beam hardening correction. The value $\Delta$, thus contains beam hardening effects that is caused by physical properties of the attenuation coefficients of bone and water, and at the same time, it also includes errors due to differential detector response to incident x-ray photons, which is the root cause of BIS artifacts.

Function $\Delta$ is addressed by two parameters, containing bone and water. A simple representation is $\Delta(p_t, p_b)$, where $p_t$, $p_b$ are the projection values of bone+water (p total), and bone only (p bone), respectively.

Similarly, the projection $p_w$ is computed corresponding to the projection through water.

Finally $p_b = p_t - p_w$ is computed where again $p_b$ is the projection value through bone. A collection of data points covering the dynamic range of the system is computed and finally, a bi-variate polynomial is fit, with $p_t$ and $p_b$ as variables. It is found that the function $\Delta(p_t, p_b)$ can be accurately captured by $\Delta(p_t, p_b) = a_0 * p_b + a_1 * p_t * p_b + a_2 * p_b * p_b + a_3 * p_b * p_b * p_t$ where $a_0$, $a_1$, $a_2$, and $a_3$ are scalars.

Now, the vector is $\Delta(p_t, p_b)$ is capable of correcting for both the low frequency and the high frequency effects of bone beam hardening at the same time. For computational efficiency, the correction may be performed without obtaining the parameter $p_t$. In order to only correct for the high frequency BIS errors, smoothing maybe performed on $a_i(det)$, (for, i=0, 3) across parameter det, where det is the detector index in a given detector row. The high frequency component of the polynomial coefficients (original vectors—smoothed vectors) contains the BIS error for each detector pixel, represented by $s_0$, $s_1$, $s_2$, $s_3$. Thus, the smoothing filter removes error related to general beam hardening (the low frequency), resulting in BIS only correction $B(p_t, p_b) = s_0*p_b + s_1*p_t*p_b + s_2 p_b*p_b + s_3*p_b*p_b*p_t$. As used herein the term low frequency refers to data representing a gradual varying function across at least ten channels, and the term high frequency refers to data representing a quickly varying function such as for every detector channel or every other detector channel.

Additionally, it was found that the $B(p_t, p_b)$ is a weak function of the parameter $p_t$. Thus, the BIS correction process can be further simplified by setting $p_t$ to a fixed value or to a more generic $P_t$. Thus, the BIS function is reduced to $B(p_t, p_b) = (s_0 + P_t*s_1) + (s_2 + P_t*s_2)*p_b*p_b = BIS_1*p_b + BIS_2*p_b*p_b$, resulting in 2 floating point coefficients per detector pixel for BIS vectors.

Once the BIS effect of individual detector pixels has been captured via spectral calibration, these "BIS calibration vectors" can then be used to correct for BIS artifacts. In order to correct for the BIS effect, the amount of bone contained in any given image needs to be measured.

The BIS Correction depends on being able to accurately determine the amount of bone seen by a given pixel and the exact detector index from which a pixel in the image was derived. In 3D Cone Beam geometry, any given pixel in an image can have contributions from several different detector rows. In order to effectively correct for the BIS artifact, the relative contribution of the different detector rows to a given image pixel needs to be computed before the correction.

Figure 3:
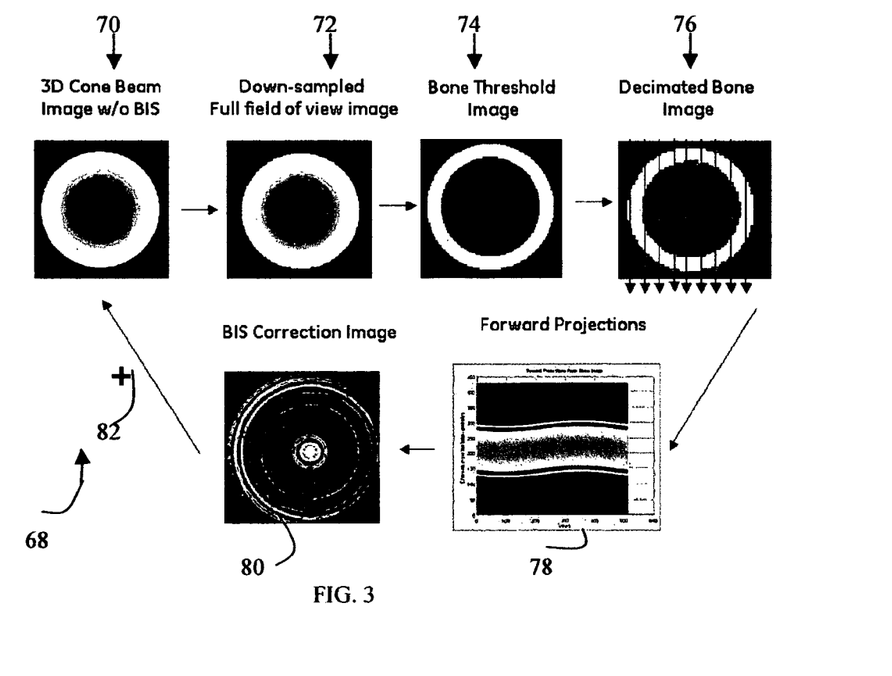
FIG. 3 illustrates a method for performing BIS correction.

FIG. 3 graphically illustrates a method 68 for BIS correction. Starting with a 3D Cone Beam image without BIS correction 70, a down-sampled full field of view (FOV) image is created at 72. The full FOV image 72 is then thresholded to obtain a bone threshold image 74. The bone threshold image 74 is then decimated at 76 to generate a plurality of forward projections that can be stacked to form a retrospective sinogram 78. The forward projections are then BIS corrected using the BIS calibration with 2 floating point coefficients per detector pixel as described above. The BIS corrected forward projections are then back projected to produce a BIS correction image 80 which is added at 82 to the uncorrected image 70 to generate a corrected image (not shown in FIG. 3).

Figure 4:
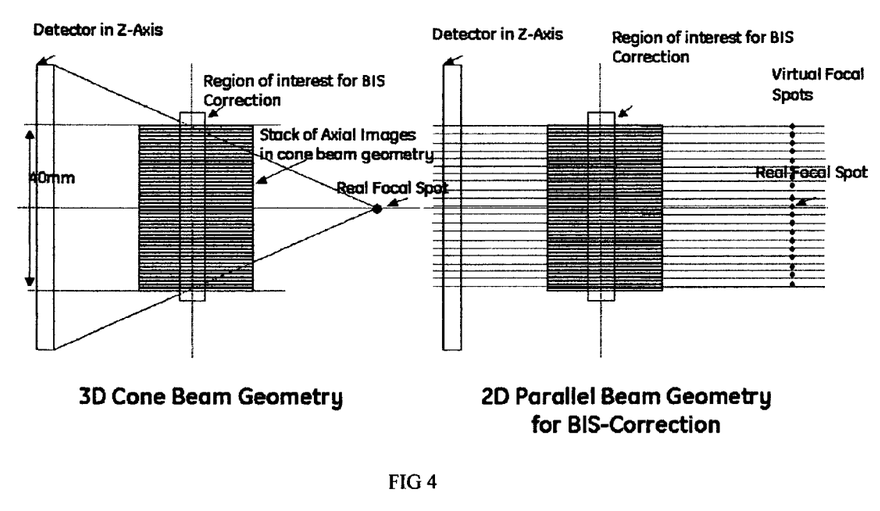
FIG. 4 illustrates the geometry used to generate the forward projections for each individual image.

Since the most sensitive region for BIS artifacts is towards the center of the detector in the channel direction, the forward projections needed for bone estimation can be performed in the 2D parallel beam geometry for computational efficiency. FIG. 4 illustrates the geometry used to generate the forward projections for each individual image. It also illustrates the need to track the exact image center such that the correct detector row of data in the true 3D cone beam geometry can be identified and matched up with the 2D parallel beam forward projections. This method can be used to accurately determine the exact detector pixel that contributed to an image pixel even in the case of views that are far away from the image plane (a common situation with outer row axial reconstructions and helical reconstructions).

Figure 5:
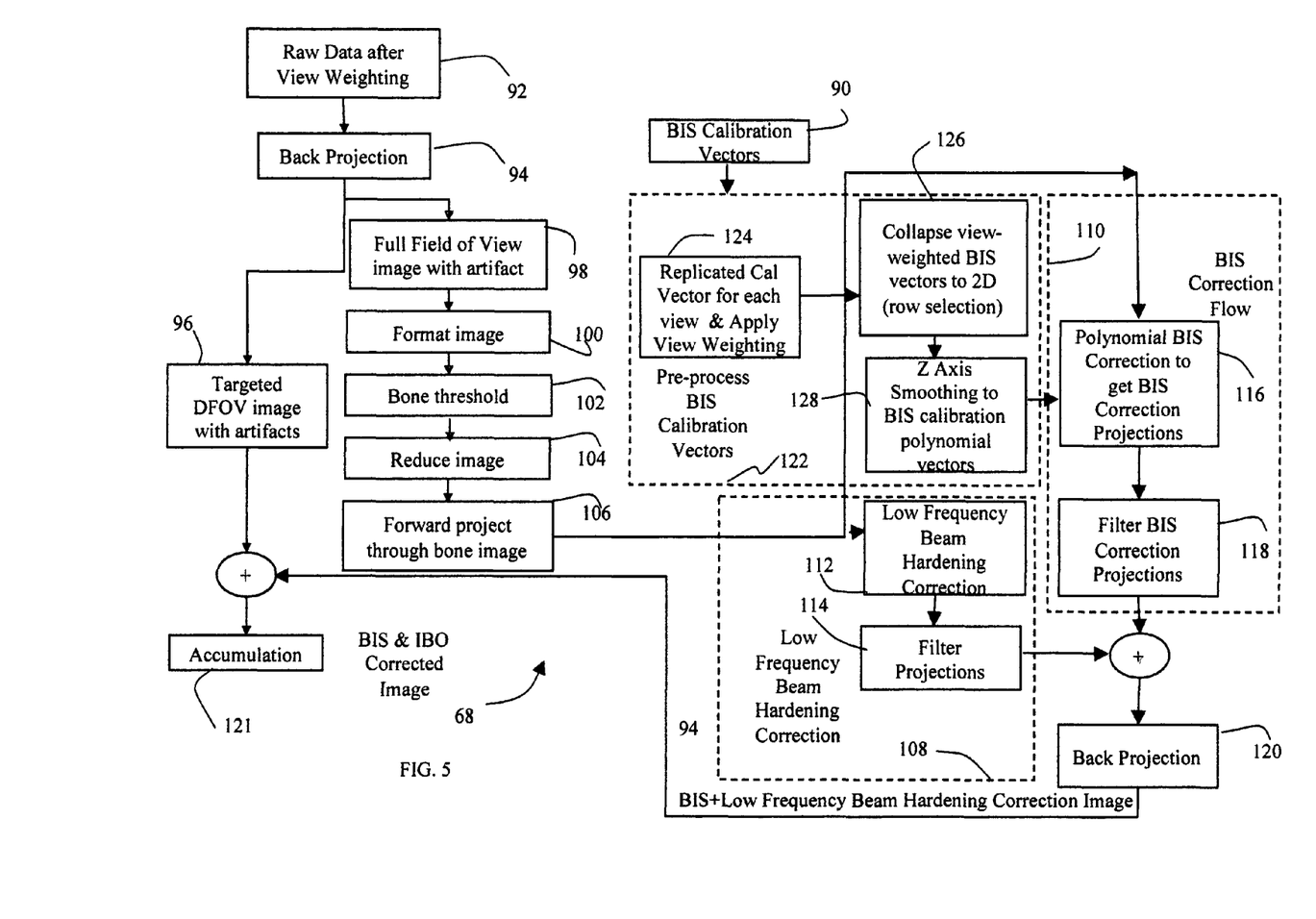
FIG. 5 illustrates the method of FIG. 3 in more detail.

FIG. 5 illustrates the method 68 of FIG. 3 in more detail. Preliminary, the BIS Calibration Vectors are calculated as described above at 90. After an imaging operation is performed, the raw data is obtained and view weighting is performed to obtain view weighted raw data at 92. The view weighted data is then back projected 94 to generate a targeted Detector FOV (DFOV) image with artifacts 96 and, in parallel, the view weighted data is back projected to generate a Full FOV image also with artifacts 98. The Full field of view image can then be formatted 100, thresholded for bone 102, and reduced 106 if desired. The image can then be forward projected 106 and the forward projections sent for low frequency beam hardening correction 108 and BIS correction 110. The low frequency correction includes low frequency beam hardening correction 112 and filtering 114 of the corrected projections. The BIS correction 110 includes the polynomial BIS correction 116 as described above and filtering 118 of the corrected projections if desired. The low frequency corrected projection and the BIS corrected projection are added together and back projection 120 generates a BIS and Low Frequency Beam Hardening Correction Image. The Correction image is then added to the DFOV image to obtain a BIS and IBO corrected image 121, wherein IBO stands for Iterative Bone Option. The corrected image 121 is also called an accumulation image because it is the accumulation of the DFOV image and the Correction image.

In one embodiment, the BIS correction uses Pre-process BIS Calibration Vectors 122 wherein Calibration Vectors are replicated for each view and view weighting 124 is performed before the view-weighted BIS vectors are collapsed 126 to 2D (row selection). Additionally, Z axis smoothing can be done to the to BIS calibration polynomial vectors 128.

One technical effect is that the herein described BIS correction uses fast iterative techniques to correct for BIS artifacts in the 3D Cone beam geometry, using the projection from bone only and the BIS vectors to obtain the correction value. The iterative correction is done in image space and the bone thresholding or segmenting is done using only the projection. It is important to note that the correction does not need access to the raw projections for correcting the image. All that is needed is access to an image. Additionally, the herein described methods and apparatus do not need the total projection length of the data (bone+water) and uses a simplified and computationally efficient approximation to correct for BIS.

Figure 6:
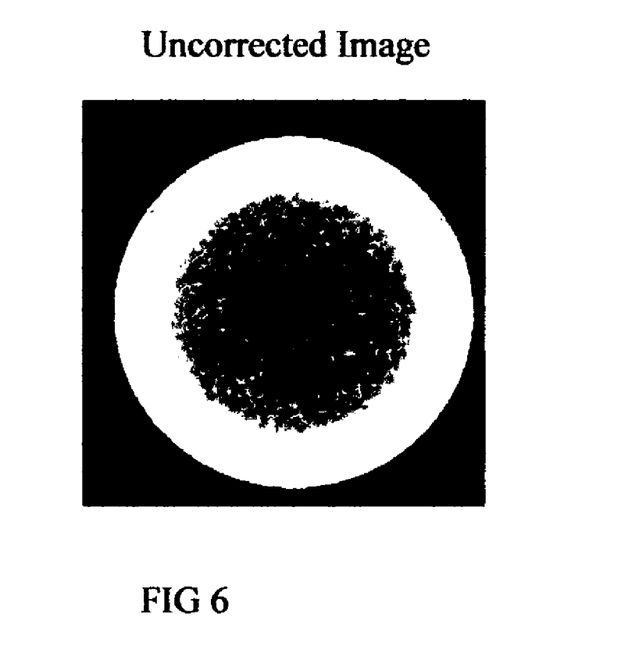
FIG. 6 illustrates an uncorrected image.
Figure 7:
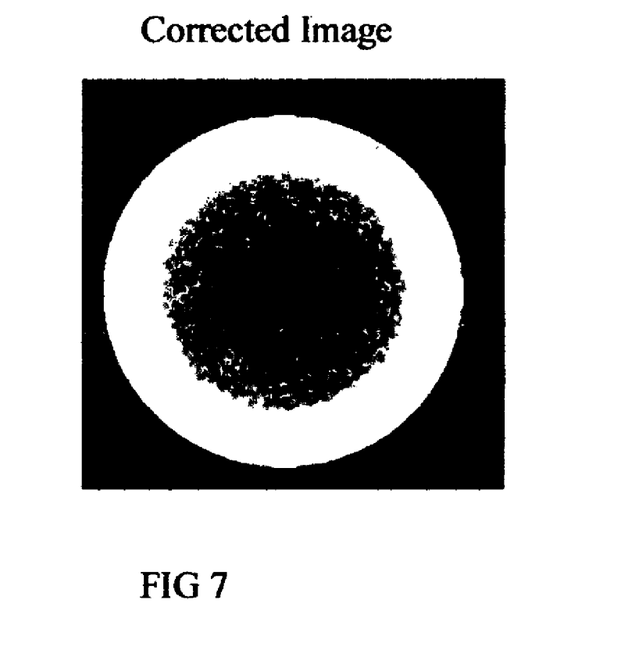
FIG. 7 illustrates a BIS corrected image.

FIG. 6 illustrates an uncorrected image and FIG. 7 illustrates a corrected image as described herein.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A CT system comprising:
    a rotatable gantry having an opening to receive a patient to be scanned;
    a high frequency electromagnetic energy projection source configured to project a cone beam of high frequency electromagnetic energy beam toward the object;
    a detector array configured to detect high frequency electromagnetic energy passing through the patient, the detector array including a plurality of detector pixels;
    a data acquisition system (DAS) connected to the detector array and configured to receive image data therefrom; and
    a computer programmed to:
        reconstruct 3D images from the image data;
        perform a bone thresholding analysis on the 3D images to generate segmented 3D images;
        determine an image center for each of the segmented 3D images;
        generate 2D parallel beam forward projections from the segmented 3D images, wherein each 2D parallel beam forward projection is generated from a respective segmented 3D image based on the image center of the respective segmented 3D image;
        apply bone-induced spectral (BIS) calibration data to the 2D parallel beam forward projections to generate BIS correction projections, the BIS calibration data comprising a pair of floating point coefficients for each detector pixel that define a BIS calibration vector representative of a BIS effect for that detector pixel; and apply a BIS correction to the 3D images based on the BIS correction projections to generate a BIS corrected image.

2. The CT system of claim 1 wherein the computer is further programmed to perform the bone thresholding analysis on the 3D images to segment the images into a low-density portion and a high density portion.

3. The CT system of claim 2 wherein the computer is further programmed to generate 2D parallel beam forward projections from the high density portion of the segmented 3D images.

4. The CT system of claim 3 wherein the high density portion of the segmented 3D images comprises bone.

5. The CT system of claim 1 wherein the computer is further programmed to:

view weight the BIS calibration vectors; and
apply a Z-axis smoothing to the BIS calibration vectors.

6. The CT system of claim 1 wherein the computer is further programmed to filter the BIS correction projections.

7. The CT system of claim 1 wherein the computer is further programmed to match detector rows of data from the 3D image with the 2D parallel beam forward projections based on the image center.

8. The CT system of claim 1 wherein the computer is further programmed to:

back-project the BIS correction projections to generate BIS artifact images; and
combine the BIS artifact images with the 3D images to generate the BIS corrected image.

9. A method for performing bone induced spectral (BIS) artifact correction comprising:

acquiring CT image data of a subject by way of a CT system;
reconstructing 3D images from the CT image data;
determining an image center for each of the 3D images;
segmenting the 3D images into a low-density portion and a high density portion;
generating 2D parallel beam forward projections from the high density portion of the segmented 3D images;
correlating detector rows of data in the high density portion of the 3D images with the 2D parallel beam forward projections based on the determined image centers;
determining bone-induced spectral (BIS) calibration vectors for each of a plurality of detector pixels, wherein each BIS calibration vectors is defined by a pair of floating point coefficients for a respective detector pixel;
applying the BIS calibration vectors to the 2D parallel beam forward projections to generate BIS correction projections; and
applying a BIS correction to the 3D images based on the BIS correction projections to generate a BIS corrected image.

10. The method of claim 9 wherein segmenting the 3D images comprises performing a bone thresholding analysis on the 3D images.

11. The method of claim 9 further comprising:

back-projecting the BIS correction projections to generate BIS artifact images; and
combining the BIS artifact images with the 3D images to generate the BIS corrected image.

12. A non-transitory computer readable storage medium having a computer program stored thereon and representing a set of instructions that, when executed by a computer, causes the computer to: receive CT image data of a subject, the CT image data comprising a plurality detector rows of data; reconstruct raw 3D images from the CT image data, each raw 3D image comprising a plurality of pixels; perform a bone thresholding analysis on the raw 3D images to generate segmented 3D images; generate 2D parallel beam forward projections from the segmented 3D images; match each of the plurality of detector rows of data from the 3D images with the 2D parallel beam forward projections; determine bone-induced spectral (BIS) calibration data for each of a plurality of detector pixels, wherein the BIS calibration data for each of the plurality of pixels is defined by a pair of floating point coefficients for a respective detector pixel; apply the bone-induced spectral (BIS) calibration data to the 2D parallel beam forward projections to generate BIS correction projections; back-project the BIS correction projections to generate BIS artifact images; and combine the BIS artifact images and the raw 3D images to generate a BIS corrected image.

13. The computer readable storage medium of claim 12 wherein the computer program further causes the computer to: determine an image center for each of the segmented 3D images; and match each of the plurality of detector rows of data from the 3D images with the 2D parallel beam forward projections based on the image centers.

14. The non-transitory computer readable storage medium of claim 12 wherein the computer program further causes the computer to perform the bone thresholding analysis on the raw 3D images to segment the raw 3D images into a low-density portion and a high density portion.

15. The non-transitory computer readable storage medium of claim 14 wherein the computer program further causes the computer to generate 2D parallel beam forward projections from the high density portion of the segmented 3D images.

16. The CT system of claim 1 wherein the pair of floating point coefficients for each detector pixel are a function of a fixed projection value of a total projection value after water hardening beam correction, $P_t$, and a computed projection value through bone, $p_b$.

17. The CT system of claim 16 wherein the computer is further programmed to determine the pair of floating point coefficients for each detector pixel according to:

$$B(p_t,p_b)=(s_0+P_t*s_1)+(s_2+P_t*s_2)*p_b*p_b$$

where $s_0$, $s_1$, and $s_2$, are a BIS error for each detector pixel, $P_t$ is a fixed value of a total projection value after water hardening beam correction, and $p_b$ is the projection value through bone.

18. The method of claim 9 further comprising determining the pair of floating point coefficients for each detector pixel according to:

$$B(p_t,p_b)=(s_0+P_t*s_1)+(s_2+P_t*s_2)*p_b*p_b$$

where $s_0$, $s_1$, and $s_2$, are a BIS error for each detector pixel, $P_t$ is a fixed value of a total projection value after water hardening beam correction, and $P_b$ is the projection value through bone.

19. The non-transitory computer readable storage medium of claim 12 wherein the computer program further causes the computer to determine a pair of floating point coefficients for each detector pixel as a function of $P_t$, and $p_b$, the pair of floating point coefficients defining a BIS calibration vector representative of a BIS effect for the respective detector pixel.

20. The non-transitory computer readable storage medium of claim 19 wherein the computer program further causes the computer to determine a pair of floating point coefficients for each detector pixel according to:

$$B(p_t,p_b)=(s_0+P_t s_1)+(s_2+P_t*s_2)*p_b*p_b$$

where $s_0$, $s_1$, and $s_2$, are a BIS error for each detector pixel.

* * * * *

UNITED STATES PATENT AND TRADEMARK OFFICE
CERTIFICATE OF CORRECTION

PATENT NO. : 7,747,057 B2  Page 1 of 1
APPLICATION NO. : 11/442450
DATED : June 29, 2010
INVENTOR(S) : Wu et al.

It is certified that error appears in the above-identified patent and that said Letters Patent is hereby corrected as shown below:

Col. 7, line 65 (Claim 12), delete "plurality detector" and substitute therefore -- plurality of detector --.

Signed and Sealed this

Thirty-first Day of August, 2010

David J. Kappos
*Director of the United States Patent and Trademark Office*